United States Patent [19]

Ishihara

[11] Patent Number: 5,507,193
[45] Date of Patent: Apr. 16, 1996

[54] PIPETTE DEVICE

[75] Inventor: Narihito Ishihara, Kanagawa, Japan

[73] Assignee: Tosoh Corporation, Yamaguchi, Japan

[21] Appl. No.: 334,393

[22] Filed: Nov. 3, 1994

[30] Foreign Application Priority Data

Nov. 4, 1993 [JP] Japan ................................. 5-275305

[51] Int. Cl.$^6$ ........................................................ B01L 3/02
[52] U.S. Cl. ................................... 73/864.24; 73/864.14
[58] Field of Search ......................... 73/864.14, 864.24, 73/864.25; 422/100; 74/20, 21, 63, 99 R, 413–415, 424.7, 424.5

[56] References Cited

U.S. PATENT DOCUMENTS

| | | | |
|---|---|---|---|
| 4,187,724 | 2/1980 | Citrin | 73/864.14 |
| 4,369,665 | 1/1983 | Citrin | 73/864.18 |
| 4,555,957 | 12/1985 | Frankel et al. | 73/864.14 |
| 5,063,790 | 11/1991 | Freeman et al. | 422/100 |

FOREIGN PATENT DOCUMENTS 0097865  4/1989  Japan ..................... 422/100

*Primary Examiner*—Robert Raevis
*Attorney, Agent, or Firm*—Sughrue, Mion, Zinn, Macpeak & Seas

[57] ABSTRACT

A pipette device capable of solving such problems as that a nozzle tip cannot be attached thereto because the device is too small in size or that an accurate drawing-in and ejection of liquids cannot be performed because a sufficient seal cannot be achieved between a shaft body lower end portion and a nozzle tip. The pipette device includes: a hollow shaft body having a lower end portion capable of being fitted into an upper end opening of a nozzle tip having the shape of an inverted cone and connected at the interior thereof to an air supply/ejection device for the drawing-in and ejection of liquids; a slide block for holding the shaft body in a manner movable up and down and rotatable about the axis thereof; a support for holding the slide block movable in an up and down direction; and a driver unit for moving the slide block up and down with respect to the support. A helical groove is formed on a part of the periphery of the upper end portion of the shaft body. The slide block has a projection adapted to mesh with the helical groove. In this pipette device, when the shaft body and the slide block are moved relative to each other in an up and down direction, the helical groove and the projection cause a rotation of the shaft body about the axis thereof.

5 Claims, 2 Drawing Sheets

PIPETTE DEVICE

BACKGROUND OF THE INVENTION

1. Field of the Invention

The present invention relates to pipette devices for transferring a predetermined amount of liquid samples such as of blood, plasma, serum, or urine from a liquid reservoir to a predetermined vessel or the like. More particularly, it relates to a pipette device of the type to be used in an automatic device for transferring a small amount of liquids for use in a so-called automatic analyzing device or the like in which the liquids are transferred automatically and successively so as to be subjected to a predetermined analysis.

2. Description of the Related Art

Transferring of liquids is conventionally performed by using a separate disposable nozzle tip (hereinafter: referred simply to as a nozzle tip) for each single operation in order to avoid contamination of the nozzle tip and of a sample by another. For its mounting and fitting, a pipette device of the type having a shaft body with a tapered lower end (becoming slender by an appropriate angle toward the terminal end) is used.

In such a device, the shaft body is pushed into an opening of a nozzle tip having the shape of an inverted cone, to achieve fitting based on friction due to the restoring force of an elastic deformation which occurs on the nozzle tip. Further, there is a device of the type for example disclosed in Japanese Utility Model Laid-Open No.63-175865, which uses the friction due to a restoring force of the elastic deformation of an O-ring provided at the terminal end of the shaft body.

In the above described conventional devices, however, a large force is necessary in order to push the shaft body into the nozzle tip to obtain a sufficient frictional force for the fitting thereof. As a result, a relatively large driver unit for the downward movement is required, where the pipette device as a whole is inevitably increased in size. Further, if a strict control is not provided on the relative position between the shaft body and the nozzle tip so as to achieve coincidence of the axis of the shaft with the center of the nozzle tip, the lower end portion of the shaft body is stopped by a nozzle tip inner wall and it cannot be brought into a close proximity with the nozzle tip however large the pushing force is. As a result, it is impossible to obtain an adequate fitting thereof and the nozzle tip cannot be mounted thereon—or a sufficient seal cannot be achieved be%ween the lower end portion of the shaft body and the nozzle tip where an accurate suction and ejection of liquids is impossible.

In the device which is provided with an O-ring, due to the softness of the O-ring, the degree of insertion of the shaft body into the nozzle tip varies depending on the force by which the shaft body is pushed into the nozzle tip. As a result, variance occurs in the relative position between the shaft body and the nozzle tip, i.e., distance from the lower end of the shaft body to the terminal end of the nozzle tip. It becomes difficult to control the relative position between the surface of the liquid to be taken in and the nozzle tip terminal end. Further, the coefficient of friction between the O-ring and the nozzle tip is relatively large. If, therefore, coincidence of the shaft axis and the center of the nozzle tip is not achieved, the O-ring is stopped at some point in its course and the nozzle tip cannot be mounted however large is the pushing force. There is also a problem relating to maintenance such as the periodical inspection and replacement of the O-ring.

SUMMARY OF THE INVENTION

As a result of an intensive investigation with respect to a pipette device especially of the type not requiring a strict control, which must be performed in the case of using a conventional device, over the relative position between the center line of the shaft body and the center line of the nozzle tip, the present inventor has achieved the present invention by finding that this can be accomplished by rotating the shaft body when inserting it into the nozzle tip. In accordance with the present invention, a pipette device includes: a hollow shaft body having a lower end portion capable of being fitted into an upper end opening of a nozzle tip having the shape of an inverted cone and connected at the interior thereof to an air supply/ejection device for the drawing in and ejection of liquids; a slide block for holding the shaft body in a manner movable up and down and rotatable about the axis thereof; a support for holding the slide block movable up and down; and a driver unit for moving the slide block up and down with respect to the support. A helical groove is formed on a part of the periphery of the shaft body. The slide block has a projection adapted to mesh with the helical groove, whereby the helical groove and the projection cause the rotation of the shaft body about the axis thereof when the shaft body and the slide block are moved relative to each other in an up and down direction.

In a further aspect of the present invention, a pipette device includes: a hollow shaft body having a lower end portion capable of being fitted into an upper end opening of a nozzle tip having the shape of an inverted cone and connected at the interior thereof to an air supply/ejection device for the drawing in and ejection of liquids; a slide block for holding the shaft body in a manner movable up and down and rotatable about the axis thereof; a support for holding the slide block movable up and down; and a driver unit for moving the slide block up and down with respect to the support; wherein the slide block has a cylindrical space the center of which coinciding with the axis of the shaft body and has a portion of the internal surface thereof formed with a helical groove; and wherein the shaft body has a projection adapted to mesh with the helical groove. Here, in the pipette device, the helical groove and the projection cause a rotation of the shaft body about the axis thereof when the shaft body and the slide block are moved up and down relative to each other. The present invention will now be described by way of the drawing.

DESCRIPTION OF THE PREFERRED EMBODIMENTS

Figure 1:
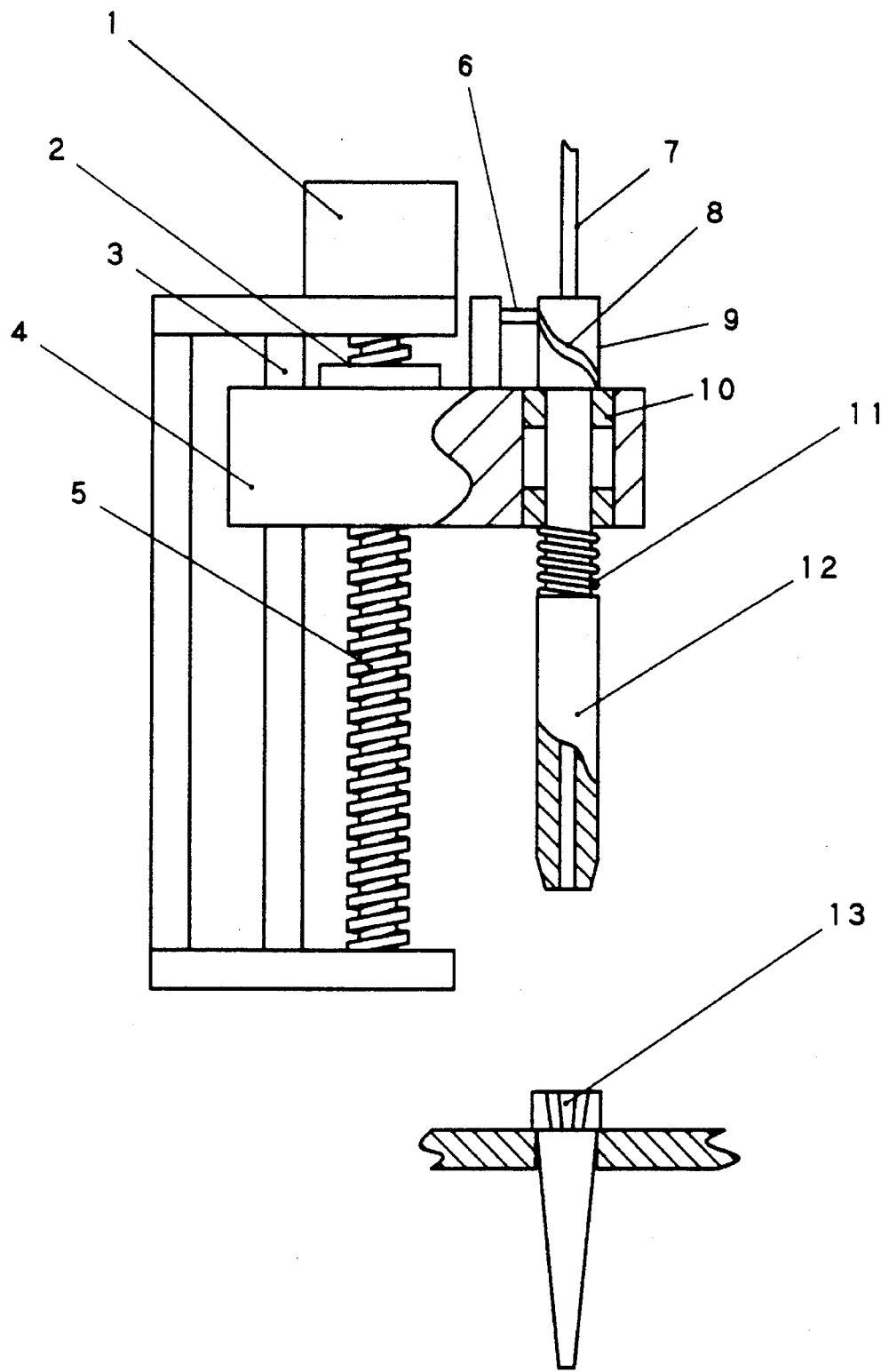
FIG. 1 shows an example of a pipette device according to the present invention.

FIG. 1 shows an example of the pipette device according to the present invention. A slender shaft body 12 having a helical groove 8 formed on a part of the outer periphery thereof is held by a slide block 4 in a manner movable up and down and rotatable about the axis thereof. In the present example, the slide block holds the shaft body through a bearing 10. A step is formed in the vicinity of the middle of the shaft body 12 and a spring 11 is disposed between this step and a lower surface of the slide block 4. Thereby, the resistance load and restoring force due to the elasticity of the spring 11 are caused when the shaft body 12 is moved in relation to the slide block 4.

Materials for forming the shaft body, slide block, etc., are not specifically limited, and metal and plastic materials such as stainless steels and polyacetal that are excellent in their wear-resisting property may typically be used. Further, in FIG. 1, the spring 11 is used for adjusting the degree of insertion (to be described later) of the shaft body 12 into the nozzle tip and for restoring the shaft body 12 to its initial position when the nozzle tip attaching operation is completed. However, an equivalent advantage may also be achieved for example by using a relatively heavy shaft body 12 instead of using the spring 11.

The lower end portion of the shaft body 12 which may be fitted into the nozzle tip is preferably tapered. While the shaft body 12 as a whole is preferably of such shape as a cylinder which will not hamper its rotational movement, its shape is not specifically limited except for the portion formed with the helical groove and the portion which is to be brought into contact with the slide block. For example, it may be a square pillar. It should be noted that a slender cylindrical shaft body 12 is especially preferable when the pipette device of the present invention is used as a pipette device for sucking a liquid from a small vessel or for discharging a liquid into a small vessel.

A hollow occurs within the shaft body 12 and one end thereof reaches the lower end portion of the shaft body 12 at which it may be fitted into an upper end opening 13 of the nozzle tip which is in the shape of an inverted cone. The other end of the internal hollow of the shaft body 12 is connected by means of an air pipe 7 to an air supply/ejection device (not shown) for sucking and discharging of liquids. The air supply/ejection device is to provide a negative pressure and a pressure to the interior of the shaft body 12, so as to draw in and eject a predetermined amount of liquid. It may typically be constituted by a syringe.

The slide block 4 is held by a support in a manner capable of being moved up and down without being rotated, by means of a driver unit which includes: a motor 1; a lead screw 5 connected to and rotated by the motor; a nut 2 conforming to the lead screw 5; and a guide bar 3 penetrating through the slide block 4. Further, the slide block 4 has a projection 6 which conforms to and is meshed with the helical groove 8 of the shaft body 12. In the present invention, instead of the above described arrangement, it is also possible to use a motor and a belt or to use an air cylinder as the driver unit.

Figure 2:
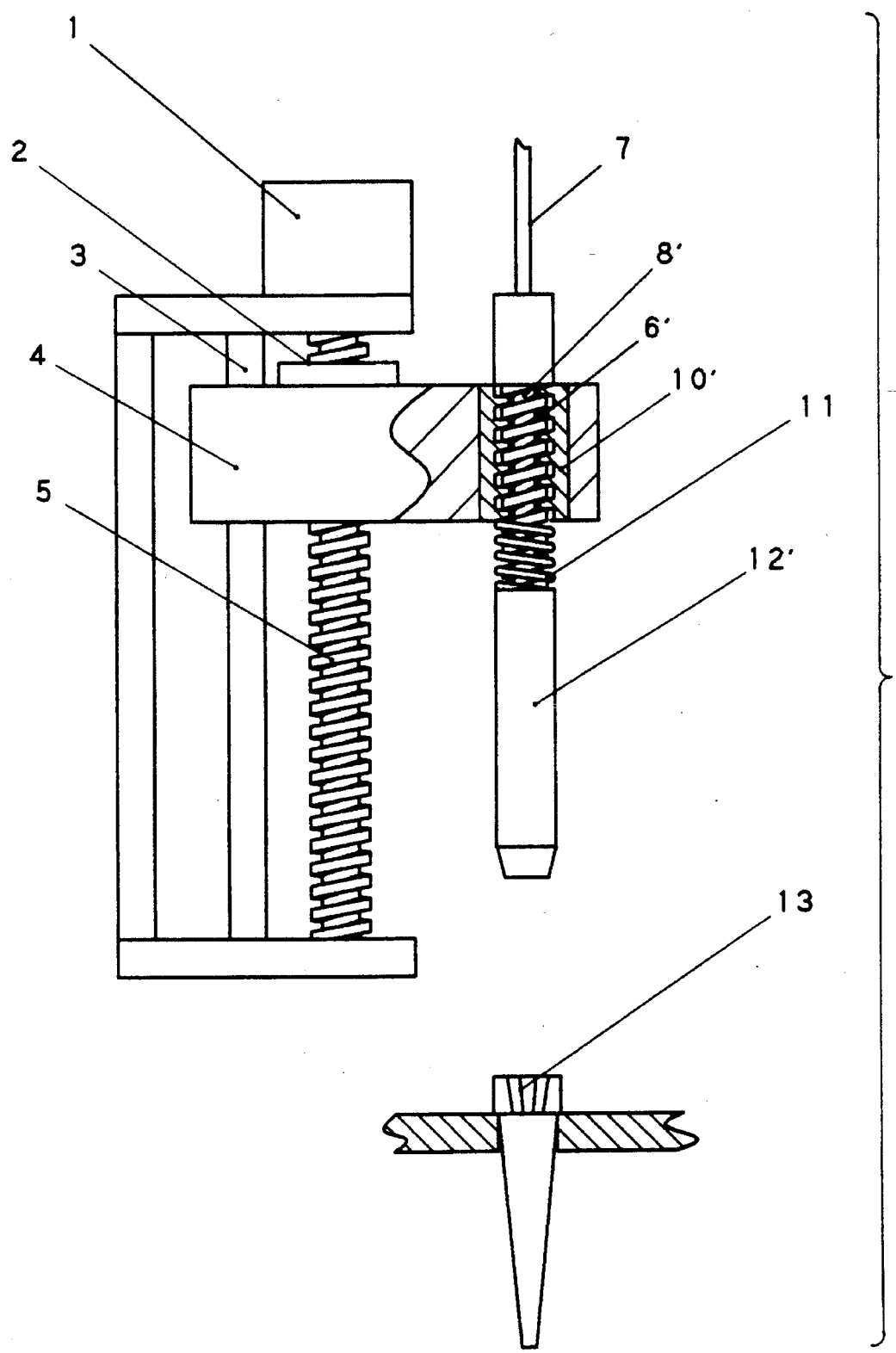
FIG. 2 shows another example of a pipette device according to the present invention.

In the present invention, the rotational movement of the shaft body may be achieved for example by the combination as shown in FIG. 1 of the helical groove 8 on the shaft body and the projection 6 on the slide block or by the combination as shown in FIG. 2 of a projection on the shaft body and a helical groove on the slide block. Here, the projection may either be a rod-like projection as shown in FIG. 1 or be a helical projection as shown in FIG. 2 corresponding to the helical groove to be combined therewith. In the example of FIG. 1, the helical groove is formed on a portion of the outer periphery of a cylindrical part 9 which is provided at an end of the shaft body.

FIG. 2 shows a device according the present invention, based on the combination of a projection on the shaft body and a helical groove on the slide block. Here, a helical groove 8' is provided on an inner side surface of a bearing 10' (a cylindrical space) which penetrates through the slide block and holds the shaft body 12' in a manner movable up and down and rotatable about the axis thereof. On the other hand, a projection 6' (a helical projection) conforming to and meshed with the helical groove is provided on the shaft body 12'.

Preferably, the projection is formed such that it is directed toward the axis of the shaft body, because its correspondence to and interlocking with the helical groove may be achieved smoothly in this way. Further, the shape of the projection is only required to correspond to the cross sectional shape of the mating helical groove. In addition to the above described helical projection, those of a hemispherical or cylindrical shape are suitably used.

In a device of the present invention having the above described construction, the slide block 4 is lowered along the guide bar 3 when the lead screw 5 is rotated by the driver unit 1. Accordingly, the shaft body 12 held on the slide block 4 is also lowered. After contacting of the end of the lower end portion of the shaft body 12 with the upper end opening of the inverted-conical nozzle tip 13, the shaft body 12 linearly moves upward in relation to the slide block 4 while applying a load due to the spring 11 to the nozzle tip 13. Here, the shaft body 12 moves upward while being rotated because of the helical groove 8 provided on the shaft body 12 and the projection 6 fixed on the slide block (see FIG. 1). After a predetermined downward movement of the slide block 4, when it is to be moved upward by reversing of the driver unit 1, the shaft body 12 returns to its original position due to the weight of itself and the force of the spring 11.

The degree of insertion of the shaft body 12 into the nozzle tip, in the example of FIG. 1, may be adjusted by the force of the spring 11 against the upward movement of the shaft body 12. In other words, when a relatively stronger spring is used, the degree of insertion of the shaft body into the nozzle tip is larger, i.e., the shaft body is inserted deeper into the nozzle tip. In the case where the weight of the shaft body, for example, is varied instead of using the spring, the shaft body is inserted deeper into the nozzle tip as the weight of the shaft body increases. In the present invention, since, unlike the conventional device, the shaft body formed of a rigid material is inserted into the nozzle tip without an intermediary of an elastic body such as an O-ring, it is possible to obtain the degree of insertion which is continuously maintained at a certain level and may be set at will based on adjusting of such as the intensity of the spring as described.

Further, a nozzle tip removing mechanism such as disclosed in Japanese Patent Application No.61-159474 may be added to the device of the present invention. Addition of such mechanism makes possible an automation of a series of operations in which a disposable nozzle tip is used and, after mounting it in a manner as described to perform drawing in and ejecting of liquids, the used disposable nozzle tip is removed.

According to the present invention, the shaft body is not simply pushed into the nozzle tip but, at the same time, it is possible to cause a rotational movement of the shaft body. The contacting angle between the shaft body and the inner wall of the upper end opening of the nozzle tip becomes smaller. Due to the principle of wedge, an elastic deformation of the nozzle tip is caused in the direction toward which the frictional force is increased. As a result, fitting of the shaft body and the nozzle tip may be strengthened and secured. Since, on the other hand, the pushing-in force may be of a small force, the driver unit may be of a smaller size. As a result, the pipette device as a whole may be reduced in size. Especially, since it is not necessary to separately provide a driving source for causing a rotational movement of the shaft body, the present invention exhibits an excellent advantage particularly in reducing the size of the device.

Furthermore, according to the present invention, even in the case where the nozzle tip is somewhat inclined with respect to the axis of the shaft body or where its center is deviated from the axis, jamming of the terminal end of the shaft body at an internal wall of the nozzle tip may be prevented by pushing in the shaft body while causing its rotational movement. As a result, it is possible to solve such problems as a failure in the mounting of the nozzle tip or a failure in achieving an accurate and ejection of liquids due to insufficient seal between the shaft body lower end portion and the nozzle tip.

What is claimed is:

1. A pipette device comprising: a hollow shaft body having a lower end portion operative for being fitted into an upper end opening of a nozzle tip having the shape of an inverted cone and connected at the interior thereof to an air supply/ejection device for drawing-in and ejection of liquids; a movable block for holding the shaft body in a manner movable in an up and down direction and rotatable about the axis thereof; a support for holding the block so as to be movable up and down; and a driver unit for moving said block up and down with respect to the support; wherein a helical groove is formed on a part of the periphery of said shaft body and said block has a projection conforming to and meshed with said helical groove, whereby said helical groove and projection cause a rotation of said shaft body about the axis thereof when the shaft body and the block are moved up and down in relation to each other.

2. A pipette device comprising: a hollow shaft body having a lower end portion operative for being fitted into an upper end opening of a nozzle tip having the shape of an inverted cone and connected at the interior thereof to an air supply/ejection device for drawing-in and ejection of liquids; a movable block for holding the shaft body in a manner movable in an up and down direction and rotatable about the axis thereof; a support for holding the block so as to be movable up and down; and a driver unit for moving said block up and down with respect to the support; wherein said block has a cylindrical space of which the center coincides with the axis of said shaft body and a portion of the internal surface of which is formed with a helical groove; and wherein said shaft body has a projection conforming to and meshed with said helical groove, whereby said helical groove and projection cause a rotation of said shaft body about the axis thereof when the shaft body and the block are moved up and down in relation to each other.

3. A pipette device according to claim 1 or 2, wherein the nozzle tip is a disposable nozzle tip.

4. A pipette device according to claim 3, further comprising a nozzle tip holding mechanism for vertically holding the nozzle tip having the shape of an inverted cone with its upper end pointing upward.

5. A pipette device according to claim 1 or 2, further comprising a nozzle tip holding mechanism for vertically holding the nozzle tip having the shape of an inverted cone with its upper end opening pointing upward.

* * * * *